(12) United States Patent
Ueda (10) Patent No.: US 9,096,846 B2
(45) Date of Patent: Aug. 4, 2015

(54) SEPARATION OF CULTURED CELLS

(75) Inventor: Masahiro Ueda, Kyoto (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 1145 days.

(21) Appl. No.: 12/645,113

(22) Filed: Dec. 22, 2009

(65) Prior Publication Data

US 2011/0151535 A1    Jun. 23, 2011

(51) Int. Cl.
*C12N 13/00* (2006.01)
*C12N 5/00* (2006.01)
*C12M 1/00* (2006.01)

(52) U.S. Cl.
CPC ............. *C12N 13/00* (2013.01); *C12M 47/04* (2013.01); *C12N 5/0081* (2013.01); *C12N 5/00* (2013.01); *C12N 2509/00* (2013.01); *C12N 2509/10* (2013.01)

(58) Field of Classification Search
None
See application file for complete search history.

(56) References Cited

U.S. PATENT DOCUMENTS

| | | | |
|---|---|---|---|
| 5,854,050 A | 12/1998 | Dalboege et al. | |
| 7,074,175 B2 * | 7/2006 | Handy et al. | 600/9 |
| 2008/0113402 A1 * | 5/2008 | McMillian | 435/29 |
| 2008/0227191 A1 | 9/2008 | Tsukada | |

FOREIGN PATENT DOCUMENTS

| | | |
|---|---|---|
| JP | 2004-000051 | 1/2004 |
| JP | 2004-236663 | 8/2004 |
| JP | 2008-228585 | 10/2008 |
| WO | WO 2007105171 A2 * | 9/2007 |
| WO | WO 2007107303 A1 * | 9/2007 |

OTHER PUBLICATIONS

Jordan, A et al. Endocytosis of dextran and silan-coated magnetite nanoparticles and the effect of intracellular hyperthermia on human mammary carcinoma cells in vitro. Journal of Magnetism and Magnetic Materials. 1999. 194: 185-196.*

Grootendorst, DJ et al. Evaluation of superparamagnetic iron oxide nanoparticles (Endorem) as a photoacoustic contrast agent for intraoperative nodal staging. Contrast Media & Molecular Imaging. 2013. 8: 83-91.*

Kunio Yagi et al., Efficient Gene Transfer With Less Cytotoxicity by Means of Cationic Multilamellar Liposomes, Biochemical and Biophysical Research Communications, Nov. 15, 1993, pp. 1042-1048, vol. 196, No. 3, Institute of Applied Biochemistry, Yagi Memorial Park, Mitake, Gifu 505-01, Japan.

Akira Ito et al., Medical Application of Functionalized Magnetic Nanoparticles, Journal O Fbioscience and Bioengineering, Jan. 11, 2005, pp. 1-11, vol. 100, No. 1, The Society for Biotechnology, Japan.

Masashige Shinkai et al., Intracellular Hyperthermia for Cancer Using Magnetite Cationic Liposomes: In vitro Study, Jpn J Cancer Res., Nov. 1996, pp. 1179-1183, Japan.

A Natsume et al., Antitumor effect and cellular immunity activation by murine interferon-B gene transfer against intracerebral glioma in mouse, Gene Therapy, 1999, pp. 1626-1633.

Culture of Human Embryonic Stem Cells (hESC). In Stem Cell Information [World Wide Web site]. Bethesda, MD: National Institutes of Health, U.S. Department of Health and Human Services, 2006, Available at http://stemcells.nih.gov/research/nihresearch/scunit/culture, 1 page.

Tjark Reblin et al., Cellular uptake of lipoprotein[a] by mouse embryonic fibroblasts via the LDL receptor and the LDL receptor-related protein, Journal of Lipid Research (1997), vol. 38, 2103-2110.

* cited by examiner

*Primary Examiner* — Allison Fox
*Assistant Examiner* — Susan E Fernandez
(74) *Attorney, Agent, or Firm* — Dorsey & Whitney LLP (57) ABSTRACT

A first cell containing at least one magnetic particle is provided and a second cell is also provided. The second cell is cultured in the presence of the first cell. An alternating magnetic field is applied to the first cell. The alternating magnetic field at least partially separates the first cell from the second cell.

20 Claims, 4 Drawing Sheets

SEPARATION OF CULTURED CELLS

BACKGROUND

A stem cell line is a family of constantly-dividing cells, the product of a single parent group of stem cells. Stem cells are typically undifferentiated cells that are obtained from human or animal tissues and can replicate for long periods of time in vitro. Embryonic stem cells (ES cells) are stem cells derived from the inner cell mass of an early stage embryo known as a blastocyst.

ES cells are of particular interest because they are pluripotent, meaning that they are able to differentiate into all derivatives of the three primary germ layers: ectoderm, endoderm, and mesoderm. When stem cells are provided with the right conditions (i.e., when provided with the right mix of cofactors and no stimuli for differentiation), ES cells can maintain their pluripotency through multiple cell divisions.

Human ES cells are typically grown on a layer of so-called "feeder cells." One example of feeder cells that are typically used are mouse embryonic fibroblasts (MEFs). MEFs adhere to the ES cells and provide enzymes, nutrients, growth factors, and other cofactors that help to maintain the human ES cells in their undifferentiated state. Without the proper culture conditions, embryonic stem cells will rapidly differentiate.

While feeder cells can be usefully employed for culturing stem cells, the stem cells typically need to be separated from the feeder cells before they can be used for implantation or other subsequent work. Current techniques (e.g., enzyme peeling or colony cutting) are labor intensive and difficult. Moreover, incomplete separation of the stem cells from the feeder cells can lead contamination of the cultured stem cells, rendering them unusable for many applications.

SUMMARY

One aspect of the methods described herein relates to the separation of cultured cells. A first cell containing at least one magnetic particle is provided and a second cell is also provided. The second cell is cultured in the presence of the first cell. An alternating magnetic field is applied to the first cell. The alternating magnetic field at least partially separates the first cell from the second cell.

According to another aspect, a device for separating cultured cells includes at least one alternating magnetic field generator that generates an alternating magnetic field. The alternating magnetic field interacts with a magnetic particle contained in a first cell to at least partially separate the first cell from a second cell. An alternating current device provides an alternating electric current to the magnetic field generator.

According to another aspect, a cell culture system includes a first cell containing at least one magnetic particle and further includes a second cell. The system includes a cell culture support that cultures at least the second cell in the presence of the first cell. An alternating magnetic field generator is coupled to the cell culture support and generates an alternating magnetic field that interacts with the at least one magnetic particle to at least partially separate the first cell from the second cell. The system further includes an alternating current device that provides an alternating electric current to the magnetic field generator.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

When different cell types are co-cultured the cells often adhere to one another. This property can make it difficult to a separate the cells if and when it is necessary to separate them for subsequent work. The methods and apparatuses described herein can be used to readily separate a second cell type from a first cell type without damaging the second cell type. These methods and apparatuses can be applied to virtually any cell type. For example, human and/or mouse cells such as embryonic stem cells, adult stem cells, and differentiated cells such as bone marrow cells, neural cells, skin cells, and cartilage cells can be cultured and subsequently separated using the methods and apparatuses described herein.

In one aspect of the embodiments described herein, a method for separating cultured cells includes providing at least a first cell containing at least one magnetic particle and at least a second cell, culturing the second cell in the presence of the first cell, and applying an alternating magnetic field to at least the first cell, the alternating magnetic field being effective to at least partially separate the first cell from the second cell.

In one aspect, the term "culturing" is used herein to refer to processes used for growing cells, particularly animal cells, in culture. Cells are typically grown in a culture container (e.g., a culture dish or a culture flask) and maintained at an appropriate temperature and gas mixture (e.g., 37° C., 5% $CO_2$ for mammalian cells) in a cell incubator. Culture conditions vary widely for each cell type, and variation of conditions for a particular cell type can result in different phenotypes being expressed.

Aside from temperature and gas mixture, the most commonly varied factor in culture systems is the growth medium. Recipes for growth media can vary in pH, glucose concentration, growth factors, and the presence of other nutrients. The growth factors used to supplement media may be derived from animal blood, such as fetal calf serum.

Cells can be grown in suspension or adherent cultures. Some cells naturally live in suspension, without being attached to a surface, such as cells that exist in the bloodstream. There are also cell lines that proliferate in suspension cultures and frequently can be grown to a higher density than adherent conditions typically allow. Adherent cells typically require a surface, such as tissue culture plastic or microcarrier, which may be coated with extracellular matrix components to increase adhesion properties and provide other signals needed for growth and differentiation. Most cells derived from solid tissues are adherent.

In one aspect, the alternating magnetic field can be a magnetic field where the polarity of the magnetic field oscillates. An alternating magnetic field can be generated using an alternating electrical current. The frequency of the magnetic field can be about 10 MHz to about 450 MHz, or about 100 MHz to about 450 MHz, or about 200 MHz to about 450 MHz. The power of the alternating magnetic field can range from about 10 W to about 250 W, or about 50 W to about 250 W, or about 50 W to about 150 W, or about 50 W to about 100 W.

In one embodiment, the source of the alternating magnetic field (e.g., an electromagnet) can be placed substantially under the container containing the cells. In another embodiment, the alternating magnetic field source can include a coil (e.g., an electrical coil) that can be placed around the culture container. In either case, the alternating magnetic field source should be placed as close to the cells as practically possible. For example, within at least about 0.1 cm, within at least about 0.5 cm, within at least about 1 cm, within at least about 1.5 cm, or within at least about 2 cm.

In one aspect, the term "separate" as used herein can refer to a number of methods and apparatuses that can be used to separate one cell type from another. For example, adherent cells typically associate (e.g. cling or adhere) with one another as well as with one or more culture surfaces. In one example, separating one cell type from another can include breaking the interactions that cause the cells to associate such that the cells are allowed to float freely in their growth media. In another example aspect, separating the one cell type from another can include breaking the interactions that cause the cells to cling together and purifying or separating one cell type from the other.

In one aspect, the term "at least partially separate" as used herein can refer to a number of processes that can be used to partially separate or partially purify one cell type from another. For example, while activating the magnetic particles discussed herein may separate cells from one or more culture surfaces and/or from adjoining cells, additional processing may be needed to "separate" or "purify" the cells. That is, the processes discussed herein may be part of a greater process needed to separate target cells from feeder cells and from one or more culture surfaces. In another example, the processes discussed herein may be sufficient to partially separate the cells from one or more culture surfaces and/or from adjoining cells such that the cells can be safely separated using physical means such as using tweezers, pipetting, filtering, cell sorting, centrifugation, using a glass capillary colony cutter, and the like.

In one aspect, embodiments of the methods and apparatuses described herein use magnetic particles for the induction of intracellular hyperthermia to accomplish at least partial separation of cells containing magnetic particles from cells that are devoid of magnetic particles. Relevant properties of appropriate magnetic particles include effective absorption of energy from an alternating magnetic field. For example, intracellular hyperthermia in the first cells can, for example, change the conformation of junctions between cells, cause the denaturation of proteins that join cells together, or cause cell death, any one of which can induce at least partial or complete separation of the first cells and the second cells. Other properties that may be included as selection criteria for the magnetic nanoparticles include, but are not limited to, nontoxicity, biocompatibility, accumulation in target cells, and limited subsequent release of nanoparticles following uptake.

The alternating magnetic field can interact with the at least one magnetic particle to generate heat inside the first cell. For example, an alternating magnetic field can cause heating of a magnetic particle through the phenomenon of hysteresis loss. Magnetic field hysteresis loss causes direct heating (i.e., the cells are heated internally) rather than generating heat in an object through transfer of heat from an external source by radiative transfer. As such, magnetic heating can be effective for heating the first cell while leaving the second cell largely unaffected. In one aspect, the heat generated in the first cell by interaction of the magnetic particle(s) with the alternating magnetic field can generate enough heat to damage or lead to cell death of the first cell. For example, damaging the cells can initiate the so-called cell death cascade. That is, many cell types typically do not "die" in a discrete event; instead, cell death follows a series of predictable events though the process of apoptosis. For example, one of the first things that occurs upon the initiation of the apoptosis process is a decrease or loss of adherence between the damaged cells and their neighbors. As such, initiating the cell death cascade (i.e., the apoptosis cascade) in the first cell can cause separation of the second cells from the first cells.

The amount of heating necessary to achieve cell death may vary according to a variety of factors including but not limited to the cell types, age or density of the culture, and amount of separation desired, among others. In an illustrative embodiment, the interaction of the magnetic particle(s) with the alternating magnetic field can heat the first cell intracellularly to a temperature in a range from about 40° C. to about 45° C., or about 42° C. to about 45° C., or about 43° C. to about 45° C. Elevating the temperature of the first cell can damage or kill the first cell. In yet another aspect, the interaction of the magnetic particle(s) in the first cell with the alternating magnetic field can heat the first cell to a temperature in a range from about 40° C. to about 45° C., or about 42° C. to about 45° C., or about 43° C. to about 45° C., while the second cell maintains a temperature in a range from about 30° C. to about 37° C. or about 34° C. to about 37° C., or about 34° C. to about 38° C., or about 36° C. to about 38° C. Elevating the temperature of the first cell as described herein can damage or kill the first cell while leaving the second cell largely unaffected, which can facilitate at least partial separation of the second cell from the second cell.

In one aspect of the methods described herein, the alternating magnetic field is maintained for a suitable period of time to accomplish the at least partial separation of cells. The length of time may vary based on a variety of factors including but not limited to, the cell types, age or density of the culture, and amount of separation desired, among others. In illustrative embodiments, times may range from about 5 seconds to about 10 minutes, or about 5 seconds to about 5 minutes, or about 10 seconds to about 5 minutes, or about 10 seconds to about 3 minutes, or about 20 seconds to about 1 minutes, or any period of time therebetween.

Embodiments of the methods described herein further include introducing the at least one magnetic particle into the first cell. That is, the at least one magnetic particle is taken up by the at least one cell and internalized into the intracellular compartment of the at least one cell. Suitable examples of methods that can be used to introduce magnetic particle(s) into the first cell include, but are not limited to, contact-mediated cellular uptake, liposomal-mediated cellular uptake, antibody-mediated cellular uptake, or electroporation, and combinations thereof. For example, magnetic particles may be coated with lipids or incorporated into liposomes to facilitate introduction of magnetic particle(s) into the first cell by endocytosis. Additional discussion of liposomic magnetic particles can be found in Kobayashi et. al, Journal of Bioscience and Bioengineering Volume 100, Issue 1, July 2005, Pages 1-11, the entirety of which is incorporated herein by reference.

In one aspect, the at least one magnetic particle can be introduced into the first cell in the absence of the second cell. In another aspect, the at least one magnetic particle can be introduced into the first cell in the presence of the second cell. In such a case, the magnetic particle(s) can be targeted to the first cell and not the second cell with the help of a targeting moiety that is recognized by the first cell and not by the second cell. A targeting moiety can, for example, include an antibody that is recognized by the first cell and that facilitates uptake (such as by endocytosis) of the magnetic particle. In another example, the targeting moiety can be a SNARE protein that can mediate of facilitate cellular uptake of the magnetic particles by complexing with another SNARE protein on the target cell. In yet another example, the targeting moiety can be a receptor protein (e.g., LDL-receptor protein) that is recognized by a cellular receptor. Additional discussion of the LDL-receptor can be found in "Cellular uptake of lipoprotein [a] by mouse embryonic fibroblasts via the LDL receptor and the LDL receptor-related protein" by Reblin et al., Journal of Lipid Research (1997), Vol. 38, 2103-2110, which is incorporated herein by reference.

In one embodiment, magnetic particles may be used to separate the first cell from the second cell without necessarily internalizing the magnetic particles in to the first cell. For example, if the magnetic particles are selectively associated with the first cells and not the second cells, hyperthermia can be induced in the first cells to cause separation of the cells. In one aspect, induction of hyperthermia in the first cells and not the second cells can be accomplished by targeting the magnetic particles to the first cells with the use of a targeting moiety that directs association between the first cells and the magnetic particles but that does not promote association between the magnetic particles and the second cells.

The first cell can be a feeder cell, which, as discussed in more detail hereinbelow, is generally a non-dividing cell that is co-cultured with a multiplying cell type for the purpose of providing growth factors, nutrients, and other co-factors to the dividing cells. Suitable examples of feeder cells include, but are not limited to, mouse embryonic fibroblast cells, mouse liver cells, zenogenetic feeder cells, allogenetic feeder cells, allogenetic fibroblast cells, artificial feeder cells, and combinations thereof.

In one aspect, the second cell can be at least one of an adherent cell (e.g., a cell that needs to adhere to a surface and/or another cell in order to grow in culture) or a stem cell. Suitable examples of adherent cells include virtually any adherent animal cell type. Suitable examples of differentiated adherent cells that can be grown in the presence of feeder cells include, but are not limited to, hematopoietic cells, mast cells, neurocytes, hepatocytes, hepatic parenchymal cells, bone marrow cells, osteoblasts, fibroblasts, and epidermal cells. Suitable examples of stem cells include, but are not limited to, pluripotent stem cells, induced pluripotent stem cells, embryonic stem cells, adult stem cells, and multipotent and induced multipotent stem cells such as neural cells, mesencymal stem cells, epithelial stem cells, bone marrow stem cells, neural stem cells, hematopoietic stem cells, germ stem cells, somatic stem cells, modified stem cells, and combinations thereof. Generally, suitable examples of second cells may be harvested from essentially any organism. For example, second cells may be harvested from a human, a cow, a pig, a mouse, a fish, or any other desired organism. Preferably, the second cells may be harvested from a human.

One embodiment includes a device for separating cultured cells. The device can include at least one alternating magnetic field generator configured to generate an alternating magnetic field and an alternating current device configured to provide an alternating electric current to the at least one magnetic field generator. Suitable examples of magnetic field generators and alternating current devices can include, but are not limited to, an electromagnet (e.g., a copper coil), direct digital synthesizers (DDS), current driver amplifiers, and magnetized coils. For example, a DDS can generate an alternating electrical current having a defined frequency to excite a magnetized coil in a current driver amplifier and thereby generate an alternating magnetic field. The required magnetic field may vary based on a variety of factors including but not limited to the cell types, age or density of the culture, and amount of separation desired, among others. In illustrative embodiments, the frequency of the magnetic field can be about 10 MHz to about 450 MHz, or about 100 MHz to about 450 MHz, or about 200 MHz to about 450 MHz. The power of the alternating magnetic field can range from about 10 W to about 250 W, or about 50 W to about 250 W, or about 50 W to about 150 W, or about 50 W to about 100 W. The alternating magnetic field can interact with the at least one magnetic particle to at least partially separate the first cell from the second cell.

The alternating magnetic field can interact with magnetic particles to induce at least partial separation of the first cell from the second cell. In another aspect, the alternating magnetic field can interact with the magnetic particles to generate heat inside the first cell. In yet another aspect, the heat generated inside the first cell can damage or kill the first cell. In yet another aspect, the at least one alternating magnetic field generator is configured to heat the first cell to a temperature in a range from about 40° C. to about 45° C., which facilitates at least partial separation of the second cell from the first cell.

In one aspect, the first cell used in conjunction with the device can be a feeder cell. Suitable examples of feeder cells include, but are not limited to, mouse embryonic fibroblast cells, mouse liver cells, zenogenetic feeder cells, allogenetic feeder cells, allogenetic fibroblast cells, artificial feeder cells, and combinations thereof.

In one aspect, the feeder cell has at least one magnetic particle contained therein. For example, the feeder cells can include about 1 mcg to about 20 mcg of magnetic particles per $cm^2$ of culture area, or about 2 mcg to about 18 mcg of magnetic particles per $cm^2$ of culture area, about 3 mcg to about 15 mcg of magnetic particles per $cm^2$ of culture area, or about 5 mcg to about 10 mcg of magnetic particles per $cm^2$ of culture area. In another aspect, the magnetic particle includes at least one of magnetite or ferrite. Magnetite is a ferrimagnetic mineral with chemical formula $Fe_3O_4$. Ferrites are a class of chemical compounds with the formula $AB_2O_4$, where A and B represent various metal cations, such as, but not limited to Fe, Mn, Co, Ni, Cu, Zn, and the like. Exampled ferrites include, but are not limited to, such as but not limited to $MnFe_2O_4$, $CoFe_2O_4$, $NiFe_2O_4$, $CuFe_2O_4$, $ZnFe_2O_4$, and the like. It is noted that magnetite is a ferrite, but not all ferrites are magnetite.

Magnetite for making magnetic particles that can be utilized according to embodiments described herein can be prepared by the addition of base to an aqueous mixture of ferrous and ferric sulfate or chloride. Also, it can be advantageous to use a mixture of $FeCl_3$ and $FeCl_2$. For example, the molar ratio of the trivalent to the divalent metal salt can be varied from about 1.0 to about 3.0, or from about 1.5 to about 2.5, and/or from about 1.8 to about 2.2. These ranges can be useful to obtain the desired size and magnetic characteristics of the magnetic particles.

Ferrites can be prepared similarly by the substitution of divalent transitional metal salts such as cobalt, manganese, nickel, zinc salts and their mixtures, for some or all of the ferrous salt. For example, ferrite formulations such as $CO_yMn_wZn_xFe_yO_4$, $Ni_yMn_wZn_xFe_yO_4$, $CO_{0.1}Mn_{0.2}Zn_{0.2}Fe_{2.5}O_{3.7}$, $Ni_{0.1}Mn_{0.2}Zn_{0.2}Fe_{2.5}O_{3.9}$, and others described in U.S. Pat. No. 4,810,401, which is incorporated herein by reference, can be obtained.

Any suitable base can be added to the aqueous mixture of the metal material. For example, ammonium hydroxide can be used when the metal is a divalent and/or trivalent iron salt.

Typically, the size of the magnetic particle grains that are incorporated into the first cell varies from about 1 to about 200 nm, or about 5 to about 150 nm, or from about 10 to about 120 nm, and/or from about 30 to about 70 nm, or any size therebetween, as measured by quasielastic light scattering. The size and material of the magnetic nanoparticles may be selected based on a variety of factors including but not limited to field strength of the magnet, cell types, age or density of the culture, and amount of separation desired, among others.

In one aspect, the second cell can be an adherent cell or a stem cell, as described in greater detail above.

One embodiment includes a cell culture system having at least a first cell containing at least one magnetic particle, at least a second cell, a cell culture support (e.g., a culture dish) configured for culturing at least the second cell in the presence of the first cell, at least one alternating magnetic field generator capable of being coupled to the cell culture support, the alternating magnetic field generator being configured to generate an alternating magnetic field capable of interacting with the at least one magnetic particle to at least partially separate the first cell from the second cell, and an alternating current device configured to provide an alternating electric current to the at least one magnetic field generator.

Suitable examples of cell culture supports can include, but are not limited to, culture containers (e.g., a petri dish), culture flasks, culture bags, culture plates, and the like. Materials of the support can be, but are not limited to, glass, quartz, polycarbonate, plastic, silicon, and the like.

In one aspect, the alternating magnetic field provided by the cell culture system can be configured to interact with the at least one magnetic particle to heat the first cell to a temperature in a range from about 40° C. to about 45° C. for a period of time sufficient to at least partially separate the first cell from the second cell.

The period of time sufficient to at least partially separate the first cell from the second cell can be in a range from about 5 seconds to about 10 minutes, about 5 seconds to about 5 minutes, about 10 seconds to about 5 minutes, about 5 seconds to about 3 minutes, about 10 seconds to about 3 minutes, about 5 seconds to about 1 minute, about 20 seconds to about 1 minute, about 5 seconds to about 45 seconds, about 5 seconds to about 30 seconds, about or about 5 seconds to about 15 seconds, or any time therebetween.

The first cell can be a feeder cell selected from a group consisting of mouse embryonic fibroblast, mouse liver cell, zenogenetic feeder cells, allogenetic feeder cells, allogenetic fibroblast cells, an artificial feeder cell, and combinations thereof. The second cell can be at least one of an adherent cell or a stem cell, as described in greater detail above.

In one embodiment, the at least one magnetic particle can include at least one of magnetite or ferrite. In this case, the magnetic particle can have a size in a range from about 5 nm to about 150 nm, or any size therebetween.

Figure 1:
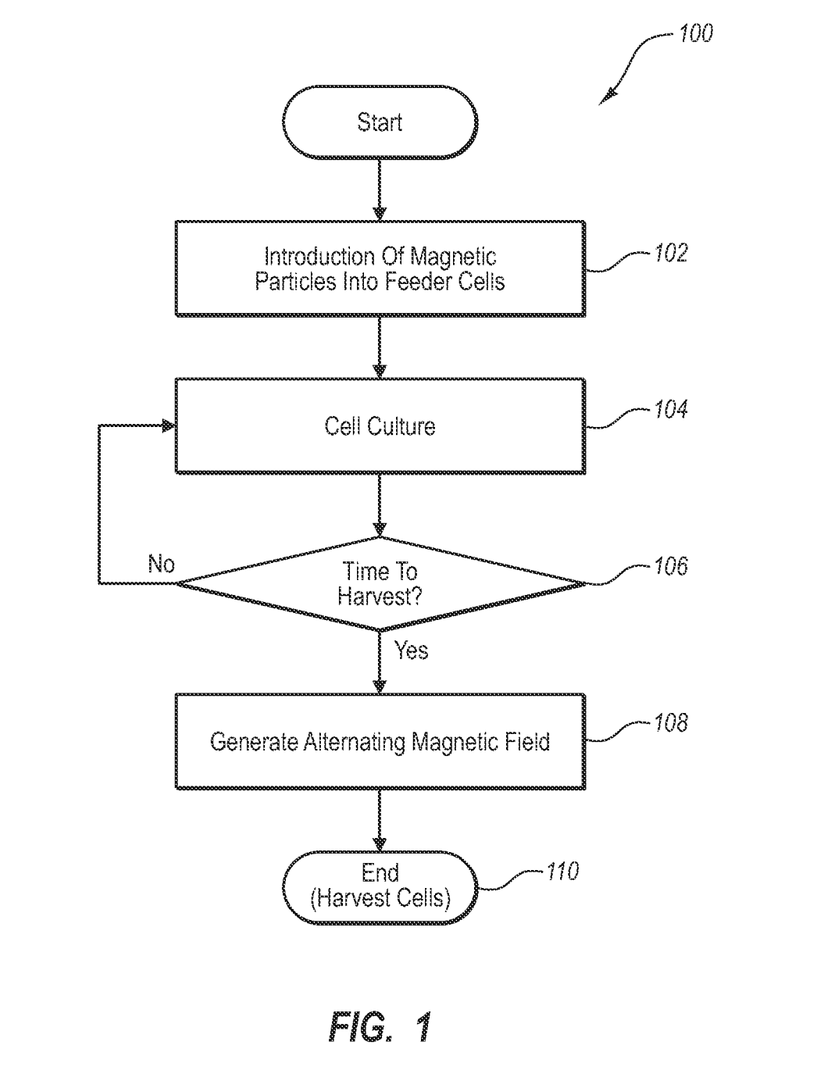
FIG. 1 is a flow diagram of an illustrative embodiment of a method for separating cultured cells from feeder cells.

Several illustrative embodiments of respective aspects of present disclosure are given blow by way of example with reference to the accompanying Figures. FIG. 1 illustrates a flow diagram of a method 100 for culturing and separation of adherent cells grown in the presence of feeder cells. In block 102, magnetic particles are introduced into feeder cells. In block 104, adherent cells are cultured in the presence of the feeder cells. In block 106, it is decided whether or not the adherent cells are ready to be harvested. If so, the adherent cells can be at least partially separated from the feeder cells in block 108 by generating an alternating magnetic field that interacts with the magnetic particles introduced in block 102. In block 110, the adherent cells are harvested. Suitable examples of harvesting methods can include, but are not limited to, using tweezers, pipetting, filtering, centrifugation, cell sorting, and the like In block 102, the introduction of magnetic particles into feeder cells can be accomplished using a number of techniques. For example, magnetic particles passively migrate into many cells types, such as reticuloendothelial cells. Efficiency of uptake can be increased by encapsulating the magnetic particles in vesicles such as magnetoliposomes. This type of vesicle includes magnetic particles wrapped in a phospholipid layer. Liposomes have structural and biokinetic advantages in that they are efficiently taken into cells by the process of endocytosis. Uptake can be further increased by manipulating surface charge, such as by imbuing the surface of the liposomes with an overall positive or negative charge. Moreover, magnetic particles can be specifically targeted to specific cell types by chemically modifying the particles or liposomes. For example, the surface of liposomes can include an antibody that is recognized by a first cell and not by a second cell. Additional discussion of uptake of magnetic particles can be found in Kobayashi et. al, Journal of Bioscience and Bioengineering Volume 100, Issue 1, July 2005, Pages 1-11 and the references discussed therein, the entirety of which is incorporated herein by reference.

In one aspect, block 104 can include culturing adherent cells in the presence of the feeder cells. There are a number of suitable cell culture protocols known in the art for culturing adherent cells in the presence of feeder cells. By way of example and not limitation, an example protocol is presented herein.

Cells (e.g., mammalian cells) are typically grown in multi-well plates. Well plates can be prepared for cell culture by coating the wells to be used with a solution of 0.1% gelatin in $diH_2O$.

A number of feeder cell types can be used including allogenetic and zenogenetic feeder cells. One common type of feeder cell used to culture human embryonic stem cells (HES cells) is mouse embryonic fibroblasts (MEF cells). MEF cells provide necessary enzymes, nutrients, growth factors, and other co-factors that are typically necessary for maintaining HES cells is a healthy and undifferentiated state.

Mouse embryonic fibroblasts are first cultured in a suitable medium (e.g., MEF media), which is a mix of DMEM (Invitrogen 11965-092), heat-inactivated FBS (Invitrogen 16000-044), non-essential amino acids (Invitrogen 11140-050) and L-Glutamine (Invitrogen 25030-081)). Feeder cells are mitotically inactivated. Suitable methods for mitotically inactivating feeder cells include, but are not limited to, treatment with 10 m/ml mitomycin C (Roche Cat #107 409) for 2 to 3 hours at 37° C. and exposure to 8000 rads of X-irradiation. Inactivated cells are washed three to four times with PBS, trypsinized (Invitrogen Cat #25300-054), and plated at a density of 0.75×105/ml with 2.5 ml per well of a gelatin-coated 6-well dish.

Prior to the addition of HES cells, MEFs are rinsed once or twice with PBS. HES cells are plated onto MEFs as small clumps in 2.5 ml per well of hESC media (e.g., DMEM/F12 A (Invitrogen 11330-032), knockout serum replacer (Invitrogen 10828-028), non-essential amino acids (Invitrogen 11140-050), L-Glutamine (Invitrogen 25030-081), and β-mercaptoethanol (Sigma 7522) containing 4 ng/ml bFGF (i.e., basic Fibroblast Growth Factor) (R&D Systems Cat #233-FB). Cells are given fresh media every day until ready they are ready for harvest. The decision associated with block 106 can be made based on the size of colonies, the age of MEFs (HES cells typically should not be older than 2 weeks), or differentiation status of the cells.

In one aspect, the generation of an alternating magnetic field in block 108 can be used to at least partially separate the feeder cells from the adherent cells (e.g., stem cells or another type of adherent cells). In one aspect, the alternating magnetic field interacts with the at least one magnetic particle to cause at least one of partial physical or partial chemical separation of the first cell from the second cell. For example, cells containing magnetic particles are attracted to the magnetic field, whereas cells devoid of magnetic particles are unaffected. The magnetic field can be used to at least partially separate the first cell from the second cell. In addition, integration with the magnetic field can cause changes to the chemical environment of the cells, either interior or exterior to the cells, which can effect at least partial separation of the first cell from the second cell.

In one aspect, the alternating magnetic field of block 108 is used in conjunction with the magnetic particles in the feeder cells for the induction of intracellular hyperthermia to accomplish at least partial separation of the adherent cells from the feeder cells. Relevant properties of magnetic particles for the induction of hyperthermia are nontoxicity, biocompatibility, high accumulation in target cells, and effective absorption of energy from an alternating magnetic field.

The alternating magnetic field of block 108 can interact with the magnetic particles introduced into the feeder cells to generate heat inside the feeder cells. In one aspect, the heat generated in the feeder cells by interaction of the magnetic particle(s) with the alternating magnetic field can generate enough heat to kill the first cell. In another aspect, the interaction of the magnetic particle(s) with the alternating magnetic field can heat the feeder cells to a temperature in a range from about 40° C. to about 45° C. In one aspect of the methods described herein, the alternating magnetic field is maintained for a period of time sufficient to effect at least partial separation of the adherent cells from the feeder cells.

Following application of the alternating magnetic field in block 108, the adherent cells can be purified away from the feeder cells by any known protocol. Suitable examples of protocols that can be used in block 110 include, but are not limited to, using tweezers, pipetting, filtering, cell sorting, centrifugation, and using a glass capillary colony cutter (i.e., if the cells are partially harvested, the cutter can dissect the cultured cell sheet), and the like.

For this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 2:
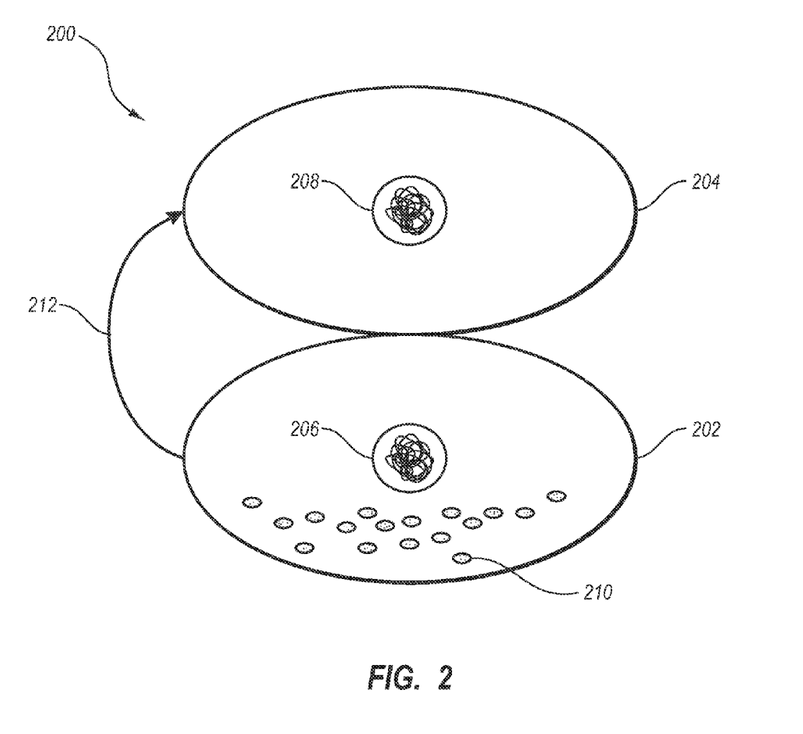
FIG. 2 illustrates a schematic diagram of a partial cutaway view of an illustrative embodiment of a feeder cell and an adherent cell.

FIG. 2 illustrates a schematic view 200 of a feeder cell 202 and an adherent cell 204, according to one embodiment. Suitable examples of feeder cells 202 are described elsewhere herein. Suitable examples of adherent cells 204 are also described elsewhere herein.

As indicated in FIG. 2, the feeder cell 202 includes a nucleus 206 and a number of magnetic particles 210 that are incorporated into the cell 202. The adherent cell 204 includes a nucleus 208 and, as shown, does not contain magnetic particles.

In one aspect, the feeder cell 202 and the adherent cell (e.g., a stem cell) 204 are co-cultured. The adherent cell 204 at least partially depends on the feeder cell. The feeder cell 202, which can be a mouse embryonic fibroblast, can synthesize an extracellular matrix that at least partially surrounds and protects the feeder cell 202 and the adherent cell 204. The extracellular matrix is an extracellular material that usually provides structural support to animal cells. The extracellular matrix usually consists of gels of polysaccharides and fibrous proteins. The feeder cell 202 also provides various substances to the adherent cell 204 that the adherent cell needs. These substances are indicated schematically by arrow 212. Substances that the feeder cell 202 provided to the adherent cell indicated at 212 can include, but are not limited to, growth factors, nutrients, and other co-factors.

The magnetic particles 210 in the feeder cell 202 are capable of interacting with an externally applied alternating magnetic field in order to effect at least partial separation of the feeder cell 202 from the adherent cell 204. As discussed in detail elsewhere herein, suitable ways in which the magnetic particles can facilitate at least partial separation of the feeder cell 202 from the adherent cell 204 include, but are not limited to, magnetic attraction and heat generation in the feeder cell.

Figure 3A:
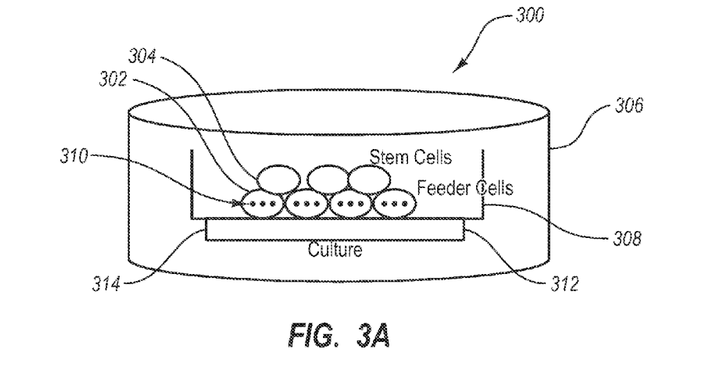
FIGS. 3A-3C provide illustrative embodiments of techniques, apparatus, and methods that can be used for separating cultured cells from feeder cells.
Figure 3B:
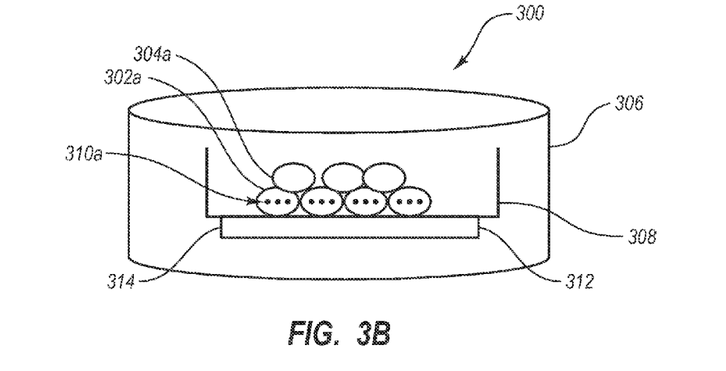
Figure 3C:
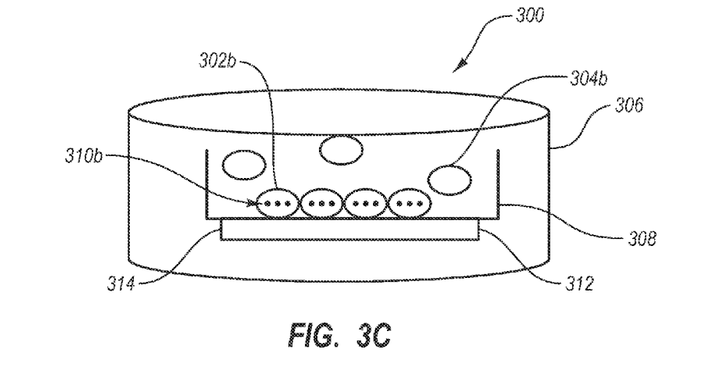

FIGS. 3A-3C illustrate a schematic view of a cell culture system 300. According to one embodiment, the cell culture system 300 includes a cell culture chamber 306 that includes a culture container 308 (e.g., a well plate or another suitable cell culture container), and an electromagnet 312 coupled to an alternating current power supply 314 for providing an alternating magnetic field in the cell culture chamber 306. Various metals can be used for the electromagnet. Suitable examples include copper (Cu), aluminum (Al), silver (Ag), and platinum (Pt), and the like or combinations thereof. Also superconductive coils such as niobium (Nb) and lead (Pb) may be used. Generally, wires can be purchased from and then made into coils with a desired number of coil turns. Alternatively, electromagnets can be purchased already manufactured As shown in FIG. 3A, the culture container 308 includes a layer of feeder cells 302 and a layer of adherent cells 304 that are adherent to the feeder cells 302. In FIG. 3A, the alternating current power supply 314 and the electromagnet 312 are not active (i.e., there is no alternating magnetic field in the cell culture chamber 306).

Referring now to FIG. 3B, to separate the feeder cells 302a from the adherent cells 304a, the alternating current power supply 314 and the electromagnet 312 are activated. Activating the alternating magnetic field can induce at least partial separation of the feeder cells 302a from the adherent cells 304a. For example, the alternating magnetic field can interact with the magnetic particles 310a to generate heat intracellularly (i.e., internal hyperthermia) in the feeder cells 302a through the phenomenon of hysteresis loss.

Referring now to FIG. 3C, the alternating magnetic field has been active for a period of time sufficient to generate enough heat to kill the feeder cells 302b. In addition, the magnetic field can continue to interact with the magnetic particles 310b in order to hold the feeder cells 302b fast to the base of culture container 308. In contrast, the cells 304b are free floating in the culture container 308 because of the loss of cell adhesion caused by the death of the feeder cells 302b. The free floating cells 304b can be purified by any means known in the art including using tweezers, pipetting, filtering, cell sorting, centrifugation, using a glass capillary colony cutter, and the like.

Figure 4:
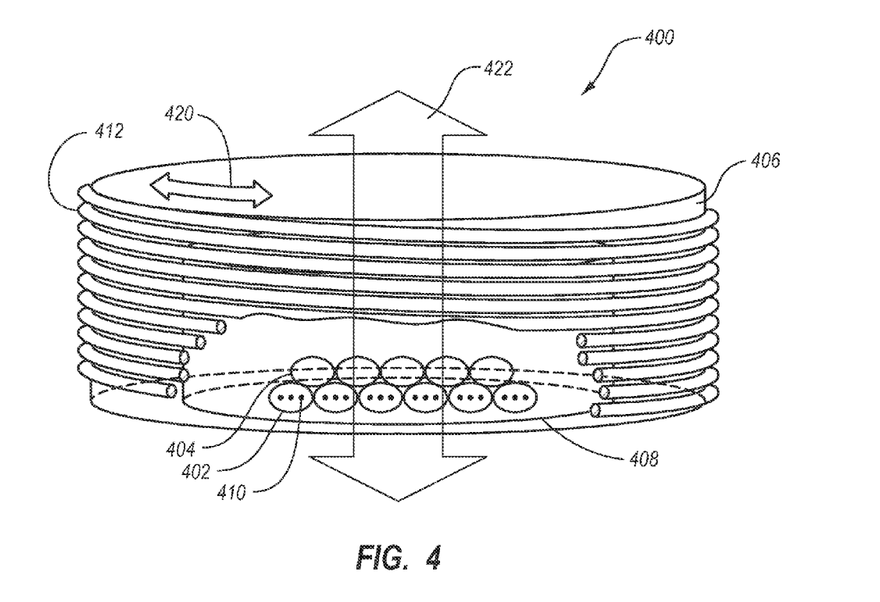
FIG. 4 is a schematic depiction of an illustrative embodiment of a cell culture system.

Referring now to FIG. 4, an embodiment of a cell culture system 400 is illustrated. According to one embodiment, the cell culture system 400 includes a cell culture chamber 406 that includes a culture container 408 (e.g., a well plate or another suitable cell culture container), and an electromagnet 412 that is coiled substantially around the culture chamber 406. As shown in FIG. 4, the culture container 408 includes a layer of feeder cells 402 and a layer of adherent cells 404 that are adherent to the feeder cells 402. As schematically illustrated in FIG. 4, the feeder cells 402 include a number of magnetic particles 410 that can interact with an alternating magnetic field to generate heat in the feeder cells 402 to effect at least partial separation of the adherent cells 404 from the feeder cells 402.

As discussed in greater detail above with respect to FIGS. 3A-3C, the feeder cells 402 can be at least partially separated from the adherent cells 404 by activating the electromagnet 412 to supply an alternating magnetic field. As shown schematically by arrows 420 and 422, supplying an alternating electrical current 420 to the coiled electromagnet 412 generates an alternating magnetic field 422 that is substantially perpendicular to the direction of electrical current flow 420.

As shown in FIG. 4, the cell culture container 408 is situated in the culture chamber 406 and the electromagnet 412 is coiled around the culture container 408. Representative dimension for the cell culture container 408 include a diameter of about 10 cm to about 20 cm, or about 10 cm to about 18 cm, about 10 cm to about 15 cm, or about 10 cm to about 12 cm. Representative dimension for the culture chamber 406 include a diameter of about 12 cm to about 20 cm, or about 12 cm to about 20 cm, about 12 cm to about 18 cm, or about 12.5 cm to about 15 cm. In any case, the electromagnet 412 should be placed as close to the cells (402 and 404) as practically possible. For example, within at least about 0.1 cm, within at least about 0.5 cm, within at least about 1 cm, within at least about 1.5 cm, or within at least about 2 cm.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for separating cultured cells, comprising:
providing a cell culture chamber including an electromagnet disposed outside of the cell culture chamber, adjacent to an exterior surface of the cell culture chamber;
positioning in contact with an interior surface of the cell culture chamber at least a first cell containing at least one magnetic particle;
culturing at least a second cell in adherence with at least the first cell;
applying an alternating magnetic field generated by the electromagnet to at least the first cell, the alternating magnetic field being effective to at least partially disassociate and separate the first cell from the second cell;
securing at least the first cell on the interior surface of the cell culture chamber; and
while at least the first cell is secured on the interior surface of the cell culture chamber, removing at least the second cell from the cell culture chamber.

2. The method of claim 1, wherein the alternating magnetic field interacts with the at least one magnetic particle to cause at least one of partial physical or partial chemical separation of the first cell from the second cell.

3. The method of claim 2, wherein the alternating magnetic field interacts with the at least one magnetic particle to generate heat inside the first cell, leading to cell death of the first cell.

4. The method of claim 3, wherein the first cell is heated to a temperature in a range from about 40° C. to about 45° C.

5. The method of claim 3, wherein the first cell is heated to a temperature in a range from about 40° C. to about 45° C. while the second cell maintains a temperature in a range from about 30° C. to about 37° C.

6. The method of claim 1, wherein the alternating magnetic field is applied for a period of time in a range from about 5 seconds to about 10 minutes.

7. The method of claim 1, further comprising introducing the at least one magnetic particle into the first cell using one or more of liposomal-mediated cellular uptake, antibody-mediated cellular uptake, or electroporation.

8. The method of claim 1, further comprising targeting the magnetic particle to the first cell using a targeting moiety recognized by the first cell and not by the second cell.

9. The method of claim 1, wherein the first cell is a feeder cell selected from a group consisting of mouse embryonic fibroblast cells, mouse liver cells, zenogenetic feeder cells, allogenetic feeder cells, allogenetic fibroblast cells, artificial feeder cells, and combinations thereof.

10. The method of claim 1, wherein the second cell is at least one of an adherent cell or a stem cell.

11. The method of claim 10, wherein the stem cell is selected from a group consisting of embryonic stem cells, mesencymal stem cells, epithelial stem cells, bone marrow stem cells, neural stem cells, hematopoietic stem cells, germ stem cells, somatic stem cells, modified stem cells, and combinations thereof.

12. A method for separating cultured cells, comprising:
providing a cell culture chamber including an electromagnet disposed outside of the cell culture chamber, the electromagnet extending around an exterior perimeter of the cell culture chamber, disposed below a bottom of the cell culture chamber, or both;
positioning at least a first cell containing at least one magnetic particle inside the cell culture chamber;
culturing, in an interior of the cell culture chamber, at least a second cell in adherence with at least the first cell;
disassociating and separating at least the second cell from at least the first cell by applying to at least the first cell an alternating magnetic field, generated by the electromagnet;
securing at least the first cell on an interior surface of the cell culture chamber; and
while at least the first cell is secured on the interior surface of the cell culture chamber, removing at least the second cell from the cell culture chamber;
wherein the alternating magnetic field is applied for a period of time in a range from about 5 seconds to about 10 minutes;
wherein the electromagnet is positioned within at least about 2 cm of the first cell but does not contact the first cell;
wherein the magnetic field exhibits a frequency in a range from about 10 MHz to about 450 MHz; and
wherein the magnetic field exhibits a power in a range from about 10 W to about 250 W.

13. The method of claim 12, wherein the electromagnet is within at least about 1.5 cm of the first cell but does not contact the first cell.

14. The method of claim 12, wherein the electromagnet is within at least about 1 cm of the first cell but does not contact the first cell.

15. The method of claim 12, wherein the electromagnet is within at least about 0.5 cm of the first cell but does not contact the first cell.

16. The method of claim 12, wherein the electromagnet is within at least about 0.1 cm of the first cell but does not contact the first cell.

17. The method of claim 12, wherein the frequency of the magnetic field is in a range from about 100 MHz to about 450 MHz.

18. The method of claim 12, wherein the frequency of the magnetic field is in a range from about 200 MHz to about 450 MHz.

19. The method of claim 12, wherein the alternating magnetic field is applied for a period of time in a range from about 20 seconds to about 1 minute.

20. The method of claim 12, wherein the power of the magnetic field is in a range from about 50 W to about 100 W.

* * * * *

UNITED STATES PATENT AND TRADEMARK OFFICE
CERTIFICATE OF CORRECTION

PATENT NO. : 9,096,846 B2  
APPLICATION NO. : 12/645113  
DATED : August 4, 2015  
INVENTOR(S) : Ueda Page 1 of 1

It is certified that error appears in the above-identified patent and that said Letters Patent is hereby corrected as shown below:

On the Title Page, insert Figure --      --.

In Column 7, Line 20, delete "$CO_yMn_wZn_xFe_yO_4$," and insert -- $CO_vMn_wZn_xFe_yO_4$, --, therefor.

In Column 9, Line 8, delete "with 10 m/ml" and insert -- with 10μg/ml --, therefor.

Signed and Sealed this  
Ninth Day of February, 2016

Michelle K. Lee  
*Director of the United States Patent and Trademark Office*